United States Patent [19]

Rupp

[11] Patent Number: 5,720,749
[45] Date of Patent: Feb. 24, 1998

[54] INTEGRAL REAMER APPARATUS WITH GUIDE COUNTERBORES IN FEMALE PRESS-FITTED PARTS

[75] Inventor: Glenn A. Rupp, Highland Lakes, N.J.

[73] Assignee: Snap-on Technologies, Inc., Lincolnshire, Ill.

[21] Appl. No.: 618,289

[22] Filed: Mar. 18, 1996

[51] Int. Cl.⁶ ............................................ A61B 17/00
[52] U.S. Cl. ............................ 606/79; 606/80; 606/180
[58] Field of Search .......................... 606/79, 80, 180

[56] References Cited

U.S. PATENT DOCUMENTS

| | | |
|---|---|---|
| 2,747,384 | 5/1956 | Beam . |
| 2,929,510 | 3/1960 | Penn . |
| 3,367,326 | 2/1968 | Frazier . |
| 3,554,192 | 1/1971 | Isberner . |
| 4,131,116 | 12/1978 | Hedrick . |
| 4,304,523 | 12/1981 | Corsmeier et al. . |
| 4,330,480 | 5/1982 | Hertel et al. . |
| 4,541,423 | 9/1985 | Barber . |
| 4,706,659 | 11/1987 | Matthews et al. . |
| 4,751,922 | 6/1988 | DiPietropolo . |
| 4,781,181 | 11/1988 | Tanguy . |
| 4,782,833 | 11/1988 | Einhorn et al. . |
| 4,813,808 | 3/1989 | Gehrke . |
| 4,880,122 | 11/1989 | Martindell . |
| 5,053,037 | 10/1991 | Lackey . |
| 5,108,405 | 4/1992 | Mikhail et al. . |
| 5,122,134 | 6/1992 | Borzone et al. . |
| 5,171,312 | 12/1992 | Salyer ............................ 606/180 |
| 5,190,548 | 3/1993 | Davis . |
| 5,230,348 | 7/1993 | Ishibe et al. . |
| 5,269,785 | 12/1993 | Bonutti . |
| 5,405,348 | 4/1995 | Anspac, Jr. et al. ............ 606/180 |
| 5,484,442 | 1/1996 | Melker et al. .................. 606/79 |

FOREIGN PATENT DOCUMENTS

| | | |
|---|---|---|
| 2366826 | 5/1978 | France . |
| 2542056 | 3/1977 | Germany . |

*Primary Examiner*—Michael Buiz
*Assistant Examiner*—Daphja Shai
*Attorney, Agent, or Firm*—Emrich & Dithmar

[57] ABSTRACT

A medullary rotational reaming apparatus includes an elongated, flexible, hollow, tubular shaft formed of a nickel-titanium alloy and having coupling portions at the opposite ends thereof. Each of a cutter head and a rotational drive coupling element has a hollow tubular coupling shank, each shank having a coupling inner surface which is quadrilobular in transverse cross section and is dimensioned to prevent free reception of a coupling portion of the shaft therein. The coupling portions of the shaft are axially press-fitted in permanent engagement, respectively, within the shanks of the cutter head and the drive coupling element, with said coupling portions being permanently deformed to the transverse cross section of the coupling inner surface of the shanks, thereby to fix the cutter head and the coupling element to the shaft solely by the press-fitted engagement of the coupling portions in the shanks.

12 Claims, 2 Drawing Sheets

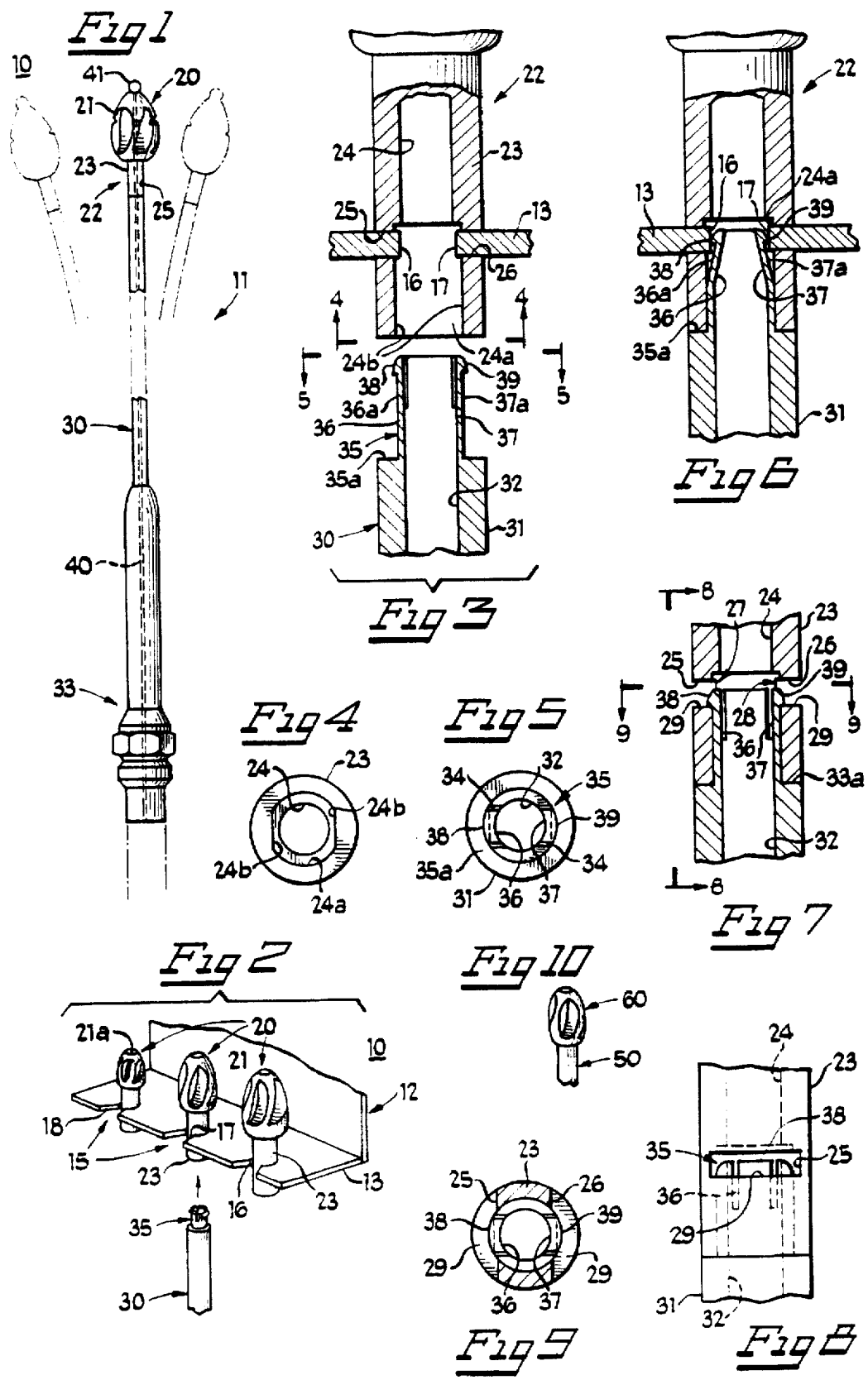

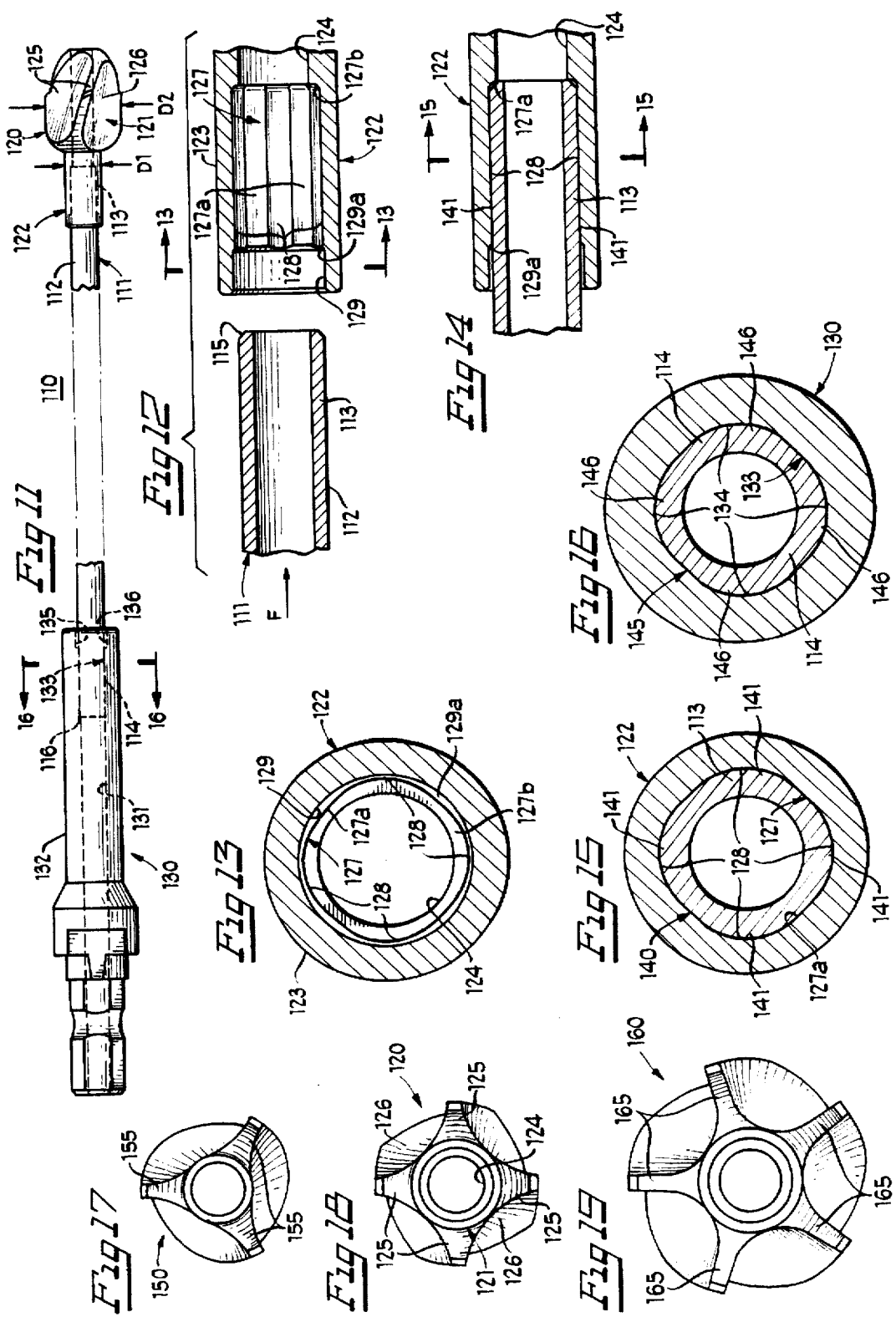

INTEGRAL REAMER APPARATUS WITH GUIDE COUNTERBORES IN FEMALE PRESS-FITTED PARTS

BACKGROUND OF THE INVENTION

1. Field of the Invention

The invention relates to medullary reaming systems and to flexible drive shafts therefor.

2. Description of the Prior Art

Medullary reamers are used to enlarge the medullary canals of bone for various reasons. The medullary canals of bone typically have some degree of curvature and, for this reason, are almost always prepared with reamers having a flexible shaft.

One type of prior flexible medullary reamer shaft consists of a spiral or helically wound metal wire or strip which comprises the shaft of the reamer. A disadvantage of this type of shaft is that the reamer can be operated only in the forward mode of rotation. If the reamer is reversed, which is occasionally necessary in order to free a lodged reamer, for example, the shaft unwinds, damaging the shaft. Another disadvantage of this spiral shaft design is that the voids between the shaft coils can trap blood and tissue, making it extremely difficult to thoroughly and properly clean and sterilize the shaft after use. Another disadvantage is that, if the cutting head experiences unusually high resistance, the driving torque will accumulate in the shaft as its coils close and then, when it overcomes the resistance to the head, will be released in a sudden burst, causing the cutting head to jump or spin ahead rapidly in an uncontrolled fashion. Such irregular movement of the cutting head may damage the bone.

Another type of medullary reamer shaft comprises a plurality of parallel, flexible elements joined together at their opposite ends by means of a welded or soldered connection. Such a shaft construction suffers from most of the same disadvantages as the helically coiled shaft described above. Another disadvantage occurs in attempting to utilize the central bore of the reamer to receive a long, small-diameter guide wire, which had previously been inserted into the medullary canal to act as a track for the advancing reamer. Except at its respective ends, this parallel-element reamer shaft lacks a well-defined and bordered central bore, making it difficult to prevent the guide wire from exiting the reamer in the area of the free standing shaft wires during the initial positioning of the guide wire within the reamer.

To overcome many of these disadvantages, there has also been provided a hollow tubular shaft formed of synthetic plastic material or a fiber-reinforced composite material. However, plastic shafts may lack the necessary torsional strength. Also, the reamer is autoclaved often and plastic will ultimately fail. A disadvantage of fiber-reinforced composite shafts is that, on failure, there is a danger that fibers will enter the blood stream.

Also, in prior medullary reamers the cutting head has been fixed to the flexible shaft by suitable welding or bonding. But those attachment techniques require additional processing or handling steps and can alter the properties of the materials of which the joined parts are formed.

SUMMARY OF THE INVENTION

It is a general object of the invention to provide an improved medullary reaming apparatus which avoids the disadvantages of prior systems while affording additional structural and operating advantages.

An important feature of the invention is the provision of a medullary reamer with a flexible drive shaft which provides uniform transmission of energy to a cutting head in forward and reverse directions and which is easy to clean.

In connection with the foregoing feature, a further feature of the invention is the provision of a reamer shaft of the type set forth which minimizes the risk of body contamination.

Still another feature of the invention is the provision of an integral reaming apparatus with a cutting head permanently fixed on a flexible reamer shaft without altering the properties of the materials of the joined parts.

In connection with the foregoing feature, another feature of the invention is the provision of a method for forming the reaming apparatus. Certain ones of these and other features of the invention are attained by providing a medullary rotational reaming apparatus comprising: an elongated flexible shaft having a coupling portion at an end thereof, and an end member having a hollow tubular coupling shank, the shank having a coupling inner surface which is non-circular in transverse cross section and is dimensioned to prevent free reception of the coupling portion therein, the coupling shank having a circularly cylindrical counterbore portion with a diameter slightly greater than the maximum transverse dimension of the coupling inner surface, and a frustoconical shoulder portion joining the counterbore to the coupling inner surface, the coupling portion being axially received in press-fitted permanent engagement within the shank with the coupling portion permanently deformed to the transverse cross section of the coupling inner surface of the shank, whereby the end member is fixed to the shaft solely by the press-fitted engagement of the coupling portion in the shank.

Still other features of the invention are attained by providing a method of forming a medullary rotational reaming apparatus including an elongated flexible shaft having coupling portions at the ends thereof and an end member having a hollow tubular coupling shank with an inner surface, the method comprising the steps of: shaping the inner surface of the coupling shank to a non-circular transverse gross section at least the minimum transverse dimension of which is less than the outer diameter of the coupling portions of the shaft, forming a circularly cylindrical counterbore in the shaped inner surface having a diameter slightly greater than the outer diameter of the coupling portion of the shaft, and press-fitting a coupling portion of the shaft axially into the shank so as to permanently deform the coupling portion of the shaft to the transverse cross-section of the inner surface of the shank, thereby to permanently fix the end member on the shaft.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIG. 1 is a fragmentary, side elevational view of a reamer of a medullary reaming system in accordance with a first embodiment of the present invention, with portions broken away and showing different positions in phantom to illustrate the flexibility of the shaft;

FIG. 2 is a fragmentary, perspective view of the support of the reaming system holding a plurality of cutting heads and illustrating insertion of the reamer shaft;

FIG. 3 is an enlarged, fragmentary view in partial vertical section showing the female connector of a cutting head held on the support with the male connector on the shaft about to be inserted;

FIG. 4 is an end view of the female connector taken along the line 4—4 in FIG. 3;

FIG. 5 is an end view of the male connector taken along the line 5—5 in FIG. 3;

FIG. 6 is a view similar to FIG. 3, illustrating the male and female connectors in their coupled condition;

FIG. 7 is a view similar to FIG. 6, illustrating the latching engagement of the male and female connectors after removal from the support;

FIG. 8 is a fragmentary, side elevational view taken along the line 8—8 in FIG. 7;

FIG. 9 is a sectional view taken along the line 9—9 in FIG. 7;

FIG. 10 is a fragmentary, perspective view of a reamer with a fixed cutting head;

FIG. 11 is a fragmentary, side elevational view of a reaming apparatus in accordance with another embodiment of the invention, with portions broken away;

FIG. 12 is an enlarged, fragmentary, sectional view showing the first stage of press-fitting the cutter head onto the shaft of the apparatus of FIG. 1;

FIG. 13 is a further enlarged, sectional view taken along line 13—13 in FIG. 12;

FIG. 14 is an enlarged, fragmentary, sectional view showing the completed press-fitted joint between the parts shown in FIG. 12; FIG. 15 is a further enlarged, sectional view taken along the line 15—15 in FIG. 14;

FIG. 16 is an enlarged, sectional view taken along the line 16—16 in FIG. 11;

FIG. 17 is an end elevational view of another cutter head of the present invention;

FIG. 18 is an enlarged, end elevational view of the cutter head of the apparatus of FIG. 1; and FIG. 19 is an end elevational view of another cutter head of the present invention.

DESCRIPTION OF THE PREFERRED EMBODIMENTS

Referring to FIGS. 1 and 2, there is illustrated a reaming system 10 in accordance with the present invention. The system 10 includes a reamer 11, comprising a cutting head 20 fixed to the end of a flexible shaft 30, and a support 12 adapted for holding a plurality of heads 20 in a support position for ready access by a user. Referring to FIG. 2, the support 12 includes a bracket 13 which may be in the form of a flat plate having a plurality of support notches 15 formed therein. Each of the notches 15 has a part-circular inner end and a pair of parallel notch edges 16 and 17 which have outwardly tapered portions 18 at their outer ends. Each of the cutting heads 20 has a head body 21, which is a toothed or fluted cutting element having an axial bore 21a therethrough. Integral with the head body 21 at its tail end is a coupling portion in the nature of a female connector 22, which is preferably in the form of a cylindrical tubular coupling shank 23. Referring also to FIGS. 3, 4 and 7, the coupling shank 23 has an axial bore 24 therethrough with an enlarged-diameter counterbore 24a at its distal end, the counterbore 24a being provided with parallel flats 24b along diametrically opposite sides thereof. Respectively formed in the coupling shank 23 at diametrically opposed locations adjacent to the flats 24b are lateral slots or grooves 25 and 26, which are formed as chords of the coupling shank 23 and are sufficiently deep to communicate with the counterbore 24a adjacent to its inner end for, respectively, defining radial apertures 27 and 28 (FIG. 7). The lower sides of the slots or grooves 25 and 26, as viewed in FIG. 7, form latch keeper shoulders 29 for a purpose to be explained more fully below.

Referring also to FIGS. 5, 6, 8 and 9, the flexible shaft 30 is in the nature of a cylindrical tubular member having a cylindrical outer surface 31 and an axial bore 32 therethrough. The shaft 30 may have any desired length, depending upon the particular application, but may typically be in the range of from 12 to 20 inches. It is a significant aspect of the invention that the shaft 30 is formed of a titanium alloy and, more specifically, of a nickel-titanium alloy of a type which has considerable flexibility. Preferably, the nickel-titanium alloy is "super elastic" alloy having a maximum recoverable strain of approximately 8%, i.e., the material can be strained up to 8% and will still elastically return to its original configuration. There results a flexible shaft 30 which has great torsional strength and yet provides the flexibility necessary for medullary reaming operations. The monolithic metal structure precludes any release of fibrous material or the like in the event of failure of the shaft. In a constructional model of the invention, the flexible shaft 30 is formed of a nickel-titanium alloy of the type sold by Raychem under the designation TINEL® Alloy BB.

The flexible shaft 30 is coupled at one end thereof by a drive coupler or adapter 33 to an associated source of rotational drive power (not shown) for rotating the shaft 30 about its axis, all in a known manner. Integral with the shaft 30 at its other end and projecting axially therefrom is a coupling structure in the nature of a male connector 35 of reduced cross-sectional area, so that the connector 35 cooperates with the adjacent end of the shaft 30 to define therebetween an annular shoulder 35a. The male connector 35 is basically cylindrical in shape and has a pair of parallel slots 34 extending thereacross at the distal end thereof as chords thereof, thereby to form two diametrically flexible arms 36 and 37, respectively having flattened outer surfaces 36a and 37a along most of their length. The flattened surfaces 36a and 37a terminate short of the distal ends of the arms 36 and 37, so as to define laterally outwardly projecting latch fingers or tabs 38 or 39, respectively, on the arms 36 and 37.

In operation, a plurality of the cutting heads 20 are preferably supported on the support 12, as illustrated in FIG. 2. The cutting heads 20 all have identical coupling shanks 23, but may have different size head bodies 21. The coupling shanks 23 are respectively received in the support notches 15. The notch edges 16 and 17 are spaced apart a distance less than the outer diameter of the coupling shank 23 and are respectively received in the lateral slots or grooves 25 and 26 of the coupling shank 23, as is best illustrated in FIGS. 2, 3 and 6. The distance between the notch edges 16 and 17 is such that, in this supported position, they will respectively extend radially inwardly of the coupling shank 23 at least as far as the flats 24b. It will be appreciated that, when the cutting heads 20 are thus supported on the support 12, they ere effectively restrained against axial movement. While, in the illustrated embodiment, the support 12 is oriented so that the supported coupling shanks 23 are disposed substantially vertically, it will be appreciated that other orientations could be used for ease of access, depending upon the particular application.

When a user wishes to attach a particular cutting head 20 to the flexible shaft 30, the male connector 35 is aligned beneath the selected cutting head 20, as illustrated in FIGS. 2 and 3, and is rotationally oriented so that the flexible arms 36 and 37 are, respectively, aligned beneath the flats 24b of the coupling shank 23. The male connector 35 is then inserted into the female connector 22 in the direction of the arrow in FIG. 2 to the coupled condition illustrated in FIG. 6, wherein the distal end of the coupling shank 23 bottoms against the shoulder 35a on the shaft 30. It will be appreciated that the arms 36 and 37 will flex to permit their insertion into the counterbore 24a of the coupling shank 23 and, as was indicated above, the support bracket 13 will firmly hold the cutting head 20 against axial movement in response to this insertion. In the coupled condition of FIG. 6, the latch fingers or tabs 38 and 39 will be respectively disposed opposite the lateral slots or grooves 25 and 26 in the coupling shank 23, but will be deflected out of those slots or grooves to an unlatching condition shown in FIG. 6, wherein they are prevented from engagement in the slots 25 and 26 by the notch edges 16 and 17 of the support bracket 13.

When the parts have been joined in the coupled condition illustrated in FIG. 6, the user then pulls the flexible shaft 30 laterally outwardly to remove the cutting head 20 from the support bracket notch 15. As the coupling shank 23 clears the notch 15, the flexible arms 36 and 37 resiliently snap back to their normal latching conditions, moving the latch fingers or tabs 38 and 39, respectively, into latching engagement with the latch keeper shoulders 29, as illustrated in FIGS. 7-9, thereby firmly latching the cutting head 20 to the flexible shaft 30.

It will be appreciated that, when it is desired to change cutting heads, the user simply moves the coupling shank 23 of the coupled cutting head 20 back into its supported position in the corresponding notch 15 in the support bracket 13. As the notch edges 16 and 17 reenter the lateral slots or groove 25 and 26 on the coupling shank 23 they deflect the flexible arms 36 and 37 back to their unlatching conditions, illustrated in FIG. 6, thereby permitting easy removal of the male connector 35 from the female connector 22 for reattachment to another cutting head 20.

It can be seen that the axial bore 32 through the flexible shaft 30 continues through the male connector 35, and the axial bore 24 through the coupling shank 23 is continuous with the axial bore 21a through the cutting head body 21. Thus, when the cutting head 20 is mounted on the flexible shaft 30, as is illustrated in FIG. 1, there is a continuous axial bore through the entire assembly, in standard fashion, for accommodating a guide wire 40. In use, as the reamer 11 is passed through a medullary canal it is slid along the guide wire 40, which has been preinserted in the canal, the guide wire 40 having an enlarged knob 41 at its distal end sized so as not to pass through the axial bore in the reamer 11, for purposes of retrieving the reamer, all in a known manner.

While, in the preferred embodiment, the gutting heads 20 are removably coupled to the flexible shaft 30, it will be appreciated that the flexible shaft of the invention could be provided with a fixed cutting head. Thus, in FIG. 10 there is shown a flexible shaft 50, which may be the same as the shaft 30 except that it lacks the male connector 35, and to which a cutting head 60 is fixedly secured by any suitable means.

Indeed, it has been found desirable in certain applications to utilize a reamer apparatus in which the cutter head is fixed to the shaft. More specifically, it has been found desirable that the ratio between the maximum outer diameter of the cutting head and the outer diameter of the shank of the cutting head be as large as possible in order to maximize the clearance space between the cutter head blades, so that the cut material can pass through these clearance channels or flutes to the rear of the cutting head. If there is insufficient clearance for pass-through of bone marrow or other tissue, the cutting head tends to act as a piston and can push the marrow out through a fracture site ahead of the cutting head. These clearance channels or flutes between the blades open at the outer surface of the cutting head shank, so that the outer diameter of the cutting head shank determines the depth of the clearance channels. Since the maximum outer diameter of the cutting head blades is determined by the size of the medullary canal to be reamed, the ratio between that diameter and the outer diameter of the cutting head shank can be varied only by varying the shank diameter. Thus, in order to maximize this ratio, the shank diameter must be minimized and, accordingly, the outer diameter of the shaft to which the shank is connected must, accordingly, be minimized. However, in the modular embodiment of FIGS. 1-9, the shank diameter must be large enough to properly accommodate the latch structure. Thus, while the shaft diameter of the modular embodiment is already smaller than in other commercially available scanners, it could be made still smaller were it not for the latch structure.

Referring now to FIGS. 11-16 and 18 there has, accordingly, been provided an integral reamer apparatus 110 including a flexible shaft 111 having permanently fixed thereto a cutting head 120 and a rotational drive coupling element 130. More particularly, the elongated flexible shaft 111 is a hollow, tubular shaft of circularly cylindrical cross section with an axial cylindrical bore therethrough and may be formed of the same material as the shaft 33, described above in connection with FIG. 1. The shaft 111 has a cylindrical outer surface 112 and has coupling portions 113 and 114, respectively, at the opposite ends thereof, these coupling portions preferably being beveled, as at 115 and 116, at the adjacent ends of the shaft 111.

The cutting head 120 includes a head body 121 provided at one end thereof with an elongated, circularly cylindrical coupling shank 122 having a cylindrical outer surface 123. An axial bore 124 is formed through the entire cutting head 120, including the body 121 and the shank 122, in a known manner. The body 121 is provided with a plurality of equiangularly spaced-apart cutting blades 125 which extend laterally outwardly and are spaced apart by clearance channels or flutes 126, the rear ends of which open at the outer surface 123 of the shank 122.

Formed inside the shank 122 is a coupling surface 127 which is non-circular in transverse cross section. The coupling surface 127 preferably has a quadrilobular share, and is formed by initially forming a counterbore 127a in the shank 122 having a diameter slightly greater than that of the axial bore 124 and slightly less than that of the outer surface 112 of the shaft coupling portions 113 and 114. Then four equiangularly spaced-apart lobes 128 are formed in the counterbore 127a. Preferably, the lobes 128 are arcuate in shape and are formed by machining the counterbore 127a of the shank 122 by any suitable process to respectively form the four lobes. The coupling surface 127 thus formed defines a shoulder 127b at its inner end where it joins the axial bore 124.

Formed in the outer end of the shank 122 is a counterbore 129 having a circular cylindrical diameter slightly greater than the maximum across-lobe transverse dimension of the coupling surface 127, and slightly greater than the outer diameter of the flexible shaft 111, being joined to the coupling surface 127 by a bevel which defines a frustoconical surface 129a.

The rotational drive coupling element 130 is similar to the drive coupler or adapter 33, described above in connection with FIG. 1, having an axial bore 131 extending therethrough and having a cylindrical outer surface 132 at the forward end thereof (the right-hand end, as viewed in FIG. 11). Formed inside the forward end of the coupling element 130 is a coupling surface 133 which is substantially identical in cross section to the coupling surface 127 described above, and is formed in the same manner, resulting in a quadrilobular cross-sectional shape including four equiangularly spaced-apart lobes 134 (see FIG. 16). Formed in the forward end of the coupling surface 133 is a circularly cylindrical counterbore 135, which is dimensioned identically to the counterbore 129, described above, in the cutting head shank 122. The counterbore 135 is beveled at its inner end, as at 136 (FIG. 11) to form a frustoconical surface defining a juncture with the coupling surface 133.

It is a fundamental aspect of the invention that the coupling portions 113 and 114 of the flexible shaft 111 are, respectively, press-fitted into engagement with the cutting shank 122 of the cutting head 120 and with the rotational drive coupling element 130. More specifically, referring to FIG. 12, in assembling the cutting head 120 on the coupling portion 113 of the shaft 111, the coupling portion 113 is first inserted into the counterbore 129 in the direction of the arrow. The dimensions of the parts permit free insertion into the counterbore 129, this insertion being aided and guided by the bevel 115 on the coupling portion 113 and a slight chamfer at the entry end of the counterbore 129. However, as was indicated above, the coupling portion 113 cannot be freely inserted into the coupling surface 127 and must be press-fitted therein. In particular, the parts are pressed together with a force F, as indicated by the arrow in FIG. 12, to force the coupling portion 113 into the coupling surface 127. The value of the force F is dependent on the relative shapes and dimensions of the parts and is sufficient to achieve a coupling with adequate torsional strength for the intended application. While the arrow implies that the cutting head 120 is held stationary, this is simply for purposes of illustration, and it will be appreciated that either part or both parts could be moved. Initial entry is facilitated by the bevel 115 on the coupling portion 113 and by the frustoconical portion 129a at the entry end of the coupling surface 127. Because of the different transverse cross-sectional shapes of the parts and the relative dimensions thereof, the outer surface of the coupling portion 113 is deformed, as at 140 (FIG. 15), to conform to the cross-sectional shape of the coupling surface 127 and fill the lobes 128. This press-fitted insertion continues until the leading end of the coupling portion 113 bottoms at the inner end of the coupling surface 127, as illustrated in FIG. 14. When the parts have thus been joined, the deformed outer surface 140 mates with the coupling surface 127 and has formed thereon lobes 141 which mateably fill the lobes 128. Thus, the parts are fixedly and permanently secured together to form a joint of great strength, having equally high torsional strength in either rotational direction of the reamer.

The coupling portion 114 at the other end of the shaft 111 is joined to the rotational drive coupling element 130 in exactly the same manner, being press-fitted into the coupling surface 133 and deformed to conform to and mate with the coupling surface 133, as indicated in FIG. 16. More particularly, the outer surface of the coupling portion 114 is deformed, as at 145, defining lobes 146 which mate with the lobes 134 of the coupling surface 133.

It is a significant aspect of the invention that, by reason of this attachment technique, the outer diameter of the coupling portions 113 and 114 of the shaft 111 and, therefore, the outer diameter of the coupling shank 122 of the cutting head 120 can be minimized. Accordingly, the ratio between the maximum outer diameter D2 of the cutting head 120 and the shank diameter D1 can be maximized. It will be appreciated that the cutting head 120 is provided in a variety of sizes to accommodate different reaming applications. For example, cutting heads might be provided with maximum outer diameters which vary from about 5 mm to about 22 mm. Since the flute depth is limited by the shank diameter of the cutting head, which is in turn limited by the shaft diameter, on small-sized cutting heads a smaller diameter shaft may be used so as to maintain a sufficient difference between the maximum outer diameter and shank diameter of the cutting head and thereby maintain adequate flute depth. In constructional models of the invention, with cutting heads having a diameter D2 from 5 mm to 7.5 mm, a flexible shaft having an outer diameter of 0.150 inch (3.8 mm) has been used, while with cutting heads having a diameter D2 from 8 mm to 22 mm, a flexible shaft with an outer diameter of 0.200 inch (5 mm) has been used. This results in ratios of D2/D1 varying from about 1.2 for the 5 mm cutting head to about 3.2 for the 22 mm cutting head.

The cutting head 120 illustrated in FIG. 11 is a four-bladed head, which is of medium size. The number of blades preferably varies, depending upon the size of the cutting head. In FIG. 17 there is illustrated a small cutting head 150 having three blades 155, while in FIG. 19 there is illustrated a large cutting head 160 having five blades 165.

In a constructional model of the invention, the cutting head 120 is formed of a suitable stainless steel, with the body 121 thereof preferably provided with a titanium nitride coating. The stainless steel material is selected so that the relative elastic properties of the parts are such that, upon insertion of the coupling portion 113 of the shaft 111 into the shank 122, the coupling portion 113 will be deformed and not the shank 122.

From the foregoing, it can be seen that there has been provided an improved reaming system which has a reamer with a flexible shaft and fixed cutting head and drive coupling element of great torsional strength, while minimizing the chance of contamination and, at the same time, optimizes the ratio between the maximum and shank outer diameters of the cutting head.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

I claim:

1. A medullary rotational reaming apparatus comprising:
   an elongated flexible shaft having a coupling portion at an end thereof, and
   an end member having a hollow tubular coupling shank, said shank having a coupling inner surface which has a transverse cross section with a maximum transverse dimension such as to prevent free reception of said coupling portion therein, said coupling shank having a circularly cylindrical counterbore portion with a diameter slightly greater than the maximum transverse dimension of said coupling inner surface, and a transition portion joining said counterbore to said coupling inner surface, said coupling portion being axially received in press-fitted permanent engagement within said shank with said coupling portion permanently deformed to the transverse cross section of the coupling inner surface of said shank, whereby said end member is fixed to said shaft solely by the press-fitted engagement of said coupling portion in said shank.

2. The apparatus of claim 1, wherein said end member is a cutter head.

3. The apparatus of claim 1, wherein said end member is a drive coupling element.

4. The apparatus of claim 1, wherein said coupling inner surface has a transverse cross section which has a multiple-lobed configuration.

5. The apparatus of claim 1, wherein said shaft is formed of a superelastic metal alloy.

6. The apparatus of claim 1, wherein said coupling inner surface is non-circular in transverse cross section.

7. The apparatus of claim 1, wherein said transition portion includes a frustoconical shoulder.

8. A medullary rotational reaming apparatus comprising: an elongated flexible shaft having first and second coupling portions respectively at opposite ends thereof;

a cutting head having a first hollow tubular coupling shank; and a rotational drive coupling element having a second hollow tubular coupling shank, each of said first and second shanks having a coupling inner surface which has a transverse cross section with a maximum transverse dimension such as to prevent free reception of said coupling portions therein, each of said coupling shanks having a circularly cylindrical counterbore portion with a diameter slightly greater than the maximum transverse dimension of said coupling inner surface, and a transition portion joining said counterbore to said coupling inner surface, said first coupling portion being axially received in press-fitted permanent engagement within said first shank with said first coupling portion permanently deformed to the transverse cross section of the coupling inner surface of said first shank, said second coupling portion being axially received in press-fitted permanent engagement within said second shank with said second coupling portion permanently deformed to the transverse cross section of the coupling inner surface of said second shank, whereby said cutting head and said rotational drive coupling element are fixed on said shaft solely by the press-fitted engagement of said coupling portions respectively in said shanks.

9. The apparatus of claim 8, wherein said coupling inner surface has a transverse cross section which has a multiple-lobed configuration.

10. The apparatus of claim 8, wherein said shaft is formed of a superelastic metal alloy.

11. The apparatus of claim 8, wherein said coupling inner surface is non-circular in transverse cross section.

12. The apparatus of claim 8, wherein said transition portion includes a frustoconical shoulder.

* * * * *